(12) United States Patent
Pantini

(10) Patent No.: US 6,541,019 B2
(45) Date of Patent: Apr. 1, 2003

(54) PRESERVATIVES OF FORMULATIONS FOR TOPICAL USE

(75) Inventor: Giovanni Pantini, Milan (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/828,212

(22) Filed: Apr. 9, 2001

(65) Prior Publication Data

US 2001/0041693 A1 Nov. 15, 2001

(30) Foreign Application Priority Data

Apr. 11, 2000 (IT) .......................... MI20A0780

(51) Int. Cl.[7] .................. A01N 25/00; A01N 57/00; A61K 31/66; C09K 3/00
(52) U.S. Cl. .................. 424/405; 252/380; 252/384; 514/129
(58) Field of Search .................. 424/405; 514/129; 252/380, 384

(56) References Cited

U.S. PATENT DOCUMENTS

| | | |
|---|---|---|
| 2,242,218 A | 5/1941 | Auer |
| 3,665,041 A | 5/1972 | Sianesi et al. |
| 3,715,378 A | 2/1973 | Sianesi et al. |
| 3,810,874 A | 5/1974 | Mitsch et al. |

FOREIGN PATENT DOCUMENTS

| | | |
|---|---|---|
| EP | 0 148 482 A2 | 7/1985 |
| EP | 0 239 123 A2 | 9/1987 |
| EP | 0 360 292 A2 | 3/1990 |
| EP | 1 074 243 A2 | 2/2001 |

OTHER PUBLICATIONS

Malinverno, G. et al., "Safety Evaluation of Perfluoropolyethers, Liquid Polymers used in Barrier Creams and other Skin–care Products," *Food and Chemical Toxicology*, vol. 34, No. 7, 1996, pp. 639–650, XP–001013353.

Primary Examiner—Jose' G. Dees
Assistant Examiner—Marina Lamm
(74) Attorney, Agent, or Firm—Arent Fox Kintner Plotkin & Kahn PLLC

(57) ABSTRACT

Use as preservative in formulations for topical use containing water of a component A): a (per)fluoropolyether phosphate of general formula:

$$R_f\text{—}[CF_2CH_2\text{—}Q\text{—}L\text{—}P(O)\,(OZ_1)\,(OZ_2)]_l \quad (I)$$

wherein l=1 or 2; L is a bivalent linking group; $Z_1$ equal to or different from $Z_2$ selected from H, alkaline or ammonium cation, di- or tri-alkanolammonium cation, di- or tri- or tetra-alkylammonium cation; $R_f$ is a (per)fluoropolyether chain having number average molecular weight in the range from about 400 to about 1,800.

12 Claims, No Drawings

PRESERVATIVES OF FORMULATIONS FOR TOPICAL USE

The present invention relates to the use of functionalized (per) fluoropolyethers as preservatives of compositions for topical use, specifically cosmetic compositions.

The maintenance in the time of the homogeneity, of the appearance and of the organoleptic properties of cosmetic formulations, as well as of the dermatological and pharmaceutical ones, is an essential requirement for the marketing of these compounds. For these reasons the use of preservatives is in many cases indispensable.

Preservatives are regulated through proper lists with indications of no use and of the allowed maximum doses. The preservative often has a local irritating and allergenic potential activity and therefore the use is limited to the minimum doses necessary to assure the compound protection from the biological contamination for the validity time of the formulation. The compositions containing water are those sensitive to the bacteria, moulds and yeasts contamination, in a proportional way to the water content. Said compositions are for example gels and emulsions and among the latter in particular oil-in-water emulsions.

The preservative must be a subsantially water-soluble compound at the concentrations at which it is used, and it must be active on a wide spectrum of microorganisms (gram-positive bacteria, gram-negative bacteria, yeasts and moulds). In general a preservative is effective only towards some kinds of microorganisms but not towards all. Therefore the activity spectrum towards the various kinds of microrganisms is enlarged by using mixtures of preservatives. Alternatively only one preservative could be used, but in this case its concentration should be increased so that the compound is B effective towards a wider spectrum of microorganisms. The drawback is that these high concentrations are generally not allowed from the rules of the various countries.

It is known that it is possible to reduce the preservative amount by adding to the formulation a surfactant amount of about 5–10% by weight. The use of surfactants has however the drawback to substantially modify the formulation and the application properties since surfactants are aggressive substances. It is well known that in cosmetic compositions the surfactants confer detergent properties wherefor for example the protective creams become detergent creams, and therefore rinsing products.

It is possible to avoid the addition of preservatives by using formulations containing high concentrations of some excipients, for example water-soluble substances, such as for example polyols, sugars, salts, etc. In these cases a partial protection is obtained, for example from bacteria but not from fungi (yeasts and moulds).

Alcohols and glycols, at high concentrations, higher than 15% by weight, can also be used. Ethanol is for example used at concentrations higher than 20% by weight. The production cost of these formulations is often high and contra-indications as for the local skin tolerability is concerned can occur.

In the prior art it is therefore known how to reduce or eliminate preservatives from the formulations of the products for topical use, in connection with their undesired local irritating or allergenic properties, by using to excipients which however have the drawback, as said, to be less effective than preservatives and to impose some restrictions as regards the formulation, or to cause in their turn skin tolerability problems.

The need was felt to formulate compositions for topical use without preservatives, in order to avoid undesired side effects at local skin level, maintaining the protection from contamination both of gram-positive and gram-negative bacteria and of yeasts and moulds, which typically requires the use of preservatives.

The Applicant has surpirisngly and unexpectedly found that it is possible to solve this technical problem by adding to said formulations for topical use containing water a well defined compound as indicated hereunder.

An object of the present invention is the use as preservative, in formulations for topical use containing water, of a component A): (per)fluoropolyether phosphate of general formula:

$$R_f-[CF_2CH_2-O-L-P(O)(OZ_1)(OZ_2)]_l \qquad (I)$$

wherein l=1 o 2;

L is a bivalent linking group, preferably of the type $(CHR_1CHR_2O)_n$ wherein $R_1$, $R_2$ equal to or different from each other are selected from H, $CH_3$; n is an integer in the range 1–50, preferably 1–6;

$Z_1$ equal to or different from $Z_2$ selected from H, alkaline or ammonium cation, di- or tri-alkanolammonium cation wherein alkanol comprises from 1 to 20 C atoms, preferably 1–4 C atoms, di- or tri- or tetra-alkylammonium cation wherein alkyl comprises from 1 to 20 C atoms, preferably 1–4 C atoms, or $R_f-CF_2CH_2-O-L-$;

$R_f$ represents a (per)fluoropolyether chain having number average molecular weight in the range from about 400 to about 1,800, preferably from 500 to 1,300, said (per)fluoropolyether chain comprising repeating units selected from one or more of the following:
a)—$(C_3F_6O)$—;
b)—$(CF_2CF_2O)$—;
c)—$(CFL_0O)$—, wherein $L_0=$—F, —$CF_3$;
d)—$CF_2(CF_2)_{z'}CF_2O$—, wherein z' is an integer 1 or 2;
e)—$CH_2CF_2CF_2O$—.

The preferred formulations comprise also:

component B): a solvent selected from linear or branched when possible alcohols, from 2 to 3 carbon atoms and ethers thereof, preferably methyl; linear or branched glycols from 2 to 6 carbon atoms or linear or branched mono alkyletherified glycols wherein the alkyl group ranges from 1 to 4 carbon atoms; dimethoxymethane, acetone.

When $R_f$ is monofunctional (l=1), an end group is of the perfluoroalkyl type such as for example $CF_3O$, $C_2F_5O$, $C_3F_7O$; optionally in perfluoroalkyl end groups one fluorine atom can be replaced by one chlorine or hydrogen atom; examples of these end groups are Cl ($C_3F_6O$), H ($C_3F_6O$).

The preferred compound of general formula (I) is the one in which $Z_1$ and $Z_2$ are different from $R_f-CF_2CH_2-O-L-$; preferably $Z_1=Z_2=$H and in the formula (I) l=2.

In particular $R_f$ is of the bifunctional (per) fluoropolyether type and it has preferably one of the following structures:

1)—$(CF_2O)_a-(CF_2CF_2O)_b-$
    with b/a comprised between 0.3 and 10, extremes included, a being an integer different from 0;
2)—$(CF_2-(CF_2)_{z'}-CF_2O)_{b'}-$
    wherein z' is an integer equal to 1 or 2;
3)—$(C_3F_6O)_r-(C_2F_4O)_b-(CFL_0O)_t-$,
    with r/b =0.5–2.0 (r+b)/t =10–30, b and t being integers different from 0;
4)—$(OC_3F_6)_r-(CFL_0O)_t-OCF_2-R'_f-CF_2O-(C_3F_6O)_r-(CFL_0O)_t-$
5)—$(CF_2CF_2CH_2)_{q'}-R'_f-O-(CH_2CF_2CF_2O)_{q'}-$
    wherein:
    $R'_f$ is a fluoroalkylene group from 1 to 4 carbon atoms;
    $L_0$ is selected between F, $CF_3$;
6)—$(C_3F_6O)_r-OCF_2-R'_f-CF_2O-(C_3F_6O)_r-$ wherein in said formulas:

—(C₃F₆O)— can represent units of formula:

—(CF(CF₃) CF₂O)— and/or —(CF₂—CF (CF₃)O)— a, b, b',q', r, t, are integers, the sum of which is such that $R_f$ shows values of number average molecular weight $\overline{M}_n$ in the range from about 400 to about 1,800, preferably 500 to 1,500.

The preferred (per)fluoropolyether chain $R_f$ is selected from the following structures:

from the bifunctional ones (l=2):

—(CF₂O)$_a$—(CF₂CF₂O)$_b$—;

—(C₃F₆O)$_r$—(C₂F₄O)$_b$—(CFL₀O$_t$—;

from the monofunctional ones (l=1):

—(C₃F₆O)$_r$—(CFL₀O)$_t$—;

wherein $L_0$ and the a,b,r,t indexes have the above indicated value, still more preferably —(CF₂O)$_a$—(CF₂CF₂O)$_b$—, wherein the a and b indexes have the above indicated values.

The compounds of formula (I) preferably used according to the present invention are those wherein L=(CH₂-CH₂O)$_n$ n being an integer from 1 to 3; $Z_1$ equal to or different from $Z_2$ is selected from H, NH₄, or an alkaline metal cation; l=2.

The compounds, according to the general formula (I), having the following formulas, are still more preferred:

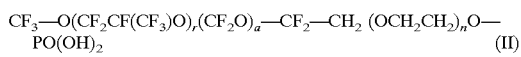

$$CF_3—O(CF_2CF(CF_3)O)_r(CF_2O)_a—CF_2—CH_2 (OCH_2CH_2)_nO—PO(OH)_2 \quad (II)$$

wherein r/a=0.5–2.0 and n=1–2;

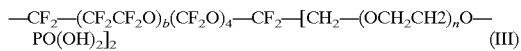

$$—CF_2—(CF_2CF_2O)_b(CF_2O)_4—CF_2—[CH_2—(OCH_2CH2)_nO—PO(OH)_2]_2 \quad (III)$$

wherein b/a=0.5–3.0 and n=1–2;

wherein a, b and r have the above mentioned meaning.

The (per)fluoropolyethers of general formula (I) are obtainable by the well known processes in the prior art, see for example the patents, herein incorporated by reference, U.S. Pat. Nos. 3,665,041, 2,242,218, 3,715,378, and EP 239,123. The functionalized fluoropolyethers having a hydroxyl termination are obtained for example according to EP 148,482, U.S. Pat. No. 3,810,874.

The preparation of the monofunctional (per) fluoropolyether phosphates of general formula (I) wherein $R_f$ has a pefluoroalkyl end group can be carried out by reacting the corresponding monohydroxy-ended (per) fluoroalkylenoxides with POCl₃. A molar ratio POCl₃/hydroxy-ended compound in the range 2/1–10/1, preferably 6/1–8/1 is used. The reaction is carried out by slowly dropping the monohydroxy-ended (per)fluoropolyether in POCl₃, at a temperature in the range 50°–100° C., preferably 70°–80° C., eliminating the HCl vapours by a KOH trap. The POCl₃ excess is removed by distillation while the formed adduct is hydrolyzed by H₂O. The hydrolyzed adduct is furtherly reacted for example with an equimolar amount of hydroxy-ended (per)fluoropolyether compound to form the monoester.

The separation of the obtained product is carried out by extraction with a suitable organic solvent, such as for example ethyl acetate. The product of formula (I) is separated from the organic phase according to known techniques, for example by evaporation of the solvent.

The preparation of the bifunctional (per)fluoropolyether phosphates (in this case $R_f$ of formula (I) has not a pefluoroalkyl end group) can be carried out by reacting the corresponding di-hydroxy-ended (per)fluoroalkylenoxides with POCl₃. A molar ratio POCl₃/hydroxy-ended compound in the range 4/1–20/1, preferably 12/1–16/1 is used. The reaction is carried out by slowly dropping the hydroxy-ended compound in POCl₃, at a temperature in the range 50°–100° C., preferably 70°–80° C., eliminating the HCl vapours by a KOH trap. The POCl₃ excess is removed by distillation while the formed adduct is hydrolyzed by H₂O. The separation of the product is carried out by extraction with an organic solvent, such as for example ethyl acetate. The product is separated from the organic phase according to known techniques, for example by evaporation of the solvent.

The (per)fluoropolyether phosphate is carried into the compositions for topical use starting from concentrated compositions comprising, besides said (per) fluoropolyether phosphate (component A) the following substances:

a solvent (component B) selected from the following: linear or branched when possible alcohols from 2 to 3 carbon atoms and methyl ethers thereof; linear or branched glycols from 2 to 6 carbon atoms or linear or branched mono alkyletherified wherein the alkyl group ranges from 1 to 4 carbon atoms; dimethoxymethane, known as methylal, acetone;

water (component C).

Component B) is preferably selected from the following: ethanol, ethylene glycol, isopropanol, propanol, acetone, methoxyethanol, propylene glycol, propan-1,2-diol, dimethoxy methane, methoxy-isopropanol, diethylene glycol, butan-1,4-diol, diethylenglycolmonoethylenether, pentan-1,2-diolo, diethylenglycol monoethylether, dipropylenglycol, dipropylenglycol monomethylether, dipropylenglycol monoethylether; still more preferably: ethanol, pentan-1,2-diol.

In said concentrated compositions the amounts of each component A), B) and C) can range from 0.01% to 70% by weight of the composition, preferably from 20% to 40% by weight, the sum A)+B)+C) being equal to 100% by weight of the concentrated composition.

Still more preferably the concentrated composition contains component A) in a percentage by weight in the range 20% –40%, component B) in the range 30–70% and water in the minimum amount required for obtaining a clear solution, and it is generally comprised between 5 and 30% by weight.

Said concentrated compositions are prepared by a process comprising the following steps:

solubilization or dispersion with partial solubilization of a (per)fluoropolyether phosphate component A) in component B) at room temperature under mild stirring;

addition, under stirring, to the mixture of water component C) initially dropwise, so that component A) does not separate, dispersing the drop so as to restore the intitial appearance of the solution before adding the subsequent aliquots of water, which can be gradually increased until completing the addition.

At the end of the addition of water a clear solution is obtained. In fact the (per)fluoropolyether phosphate as such is not soluble in water but the mixture of the perfluoropolyether phosphate with component B) is on the contrary dilutable with water.

The added water is preferably at a temperature in the range 50° C.–60° C.

The concentrated solution is then diluted, as indicated in the Examples, with solvents and/or excipients to give the compositions for topical use.

The compositions for topical use contain the preserving system comprising the component A) (per)fluoropolyether phosphate of formula (I) in a percentage by weight in the range 0.01–10%, preferably 0.5–5%, still more preferably 0.5–2%.

Tests carried out by the Applicant have shown that the (per) fluoropolyether phosphate of formula (I) is effective towards gram-positive, gram negative bacteria, yeasts or mono-cellular fungi. It has been found that when the molecular weight of the fluorinated chain $R_f$ is 2,000 the compound is no longer active as a preservative and therefore it cannot be used for the specific use of the present invention.

In the final formulations for topical use the amounts of component B) are reduced, and anyway such as not to result effective in absence of the (per)fluoropolyether phosphate of formula (I).

The concentrations by weight of component B) are generally the same above mentioned for the (per) fluoropolyether phosphate of formula (I).

Preferably in formulations for topical use a 1:1 ratio by weight between the solvent component B) and the (per) fluoropolyropolyether phosphate of formula (I) component A) is used.

Preferably in the compositions for topical use component B) is selected between ethyl alcohol and pentan-1,2-diol, more preferably pentan-1,2-diol.

In the compositions according to the invention preferably the amount of perfluoropolyether phosphate of formula (I) component A) and of solvent component B) is in the range 0.5–2%.

The use that is the object of the present invention is achieved by carrying the (per)fluoropolyether phosphate of formula (I) in the above described concentrated solutions and then diluting with solvents and/or excipients in order to obtain the formulations for topical use containing the above indicated amounts of (per)fluoropolyether phosphate of formula (I).

The following Examples are given for illustrative purposes and they are not limitative of the scope of the invention.

EXAMPLE 1

Test for Evaluating the Antimicrobic Activity

The test consists in contaminating the product with microorganisms of different species, following then the growth or the destruction thereof in the time, so as to evaluate the efficacy of the preserving system. The product to be tested is contaminated with gram-positive and gram-negative bacteria, and monocellular fungi, so as to have the presence of the microorganisms which can more easily contaminate a preparation for topical use, i.e. the most diffused ones.

The product is fractionated in aliquots of 100 g each, each aliquot is added of one of the microorganisms selected for the contamination. The inoculum, titred at about 108 cells, is homogeneously dispersed in the formulation.

The contamination measure is made by counting the microorganism colonies at different times (at 0 time (relly within twenty minutes), after 24 hours, 7 days, 14 days and 28 days), starting from the contamination, maintaining in the meantime the sample in the dark at a temperature in the range 20–25° C.

In order to effect the microorganism counting a 1 ml aliquot of the contaminated sample is taken, which is diluted 1 to 10 by distilled water (by double reverse osmosis) additived with Tween 80 at a concentration 1.5% by weight under sterile conditions. The suspension is transferred into a Petri capsule, to which an amount comprised beteen 15 and 20 ml of agar soil (Tryptone Soya Agar (Unipath) is added. The agar soil is initially maintained at a temperature of 45° C. so as it is liquid. Then it is let solidify and the capsule is turned upside down to avoid the water condensate.

The Petri capsules are incubated at about 30° C. for 48–72 hours for the bacteria counting and at 20–25° C. for about 5 days for the monocellular fungi counting. It is considered inhibition when the number of the microorganisms results lower than 100, and there is not a subsequent increase. The result can be expressed as UFC/g (Units Forming colony/gram). Since they are diluted aqueous suspensions, the results can indifferently be expressed as UFC/g or UFC/ml. In order to determine the concentration it will then be necessary to take into account the various dilutions, wherefore it is necessary to consider a logarithmic scale. The first dilution 1 to 10 (with the use of a diluent as above described) is necessary to stop the preservative activity. Therefore when it is reported in the results that UFC/g<10 it does not mean that the system is absolutely sterile, but that the sensitivity limit of the method has been reached. The subsequent dilutions, always in the 1:10 ratio, which are necessary to bring the concentration of the cells under 10/ml, give the measure of the initial concentration of the cells, which therefore will then be expressed by a number (lower than 10) multiplied by a 10th power.

The kinds of microorganisms are the following:

*Escherichia coli* (ATCC 25922 stock): gram-negative bacterium of human type, present in the intestine and spread through the faeces;

*Stafilococcus aureus* (ATCC 25923 stock): gram-positive bacterium of human type spread on the body; it is the one which more often contaminates a preparation for topical use when utilized by the user;

*Pseudomonas aeruginosa* (ATCC 27853 stock): gram-negative bacterium spread in the environment (for example in sinks), which can multiply also in bidistilled water.

*Candida albicans* (ATCC 10231 stock): unicellular fungus.

It is a microorganism which for its sizes, differently from the moulds which are multicellular fungi, escapes the visual observation.

EXAMPLE 2

Formulation Gel

A gel for the hand protection based on xanthan rubber has been prepared by the following procedure:

A solution is prepared at 50% of perfluoropolyether phosphate of formula (I) having a molecular weight of the perfluorinated chain of 1200 (Fomblin® HC/P2–1000) component A) in ethanol component B), to which a water amount is added so as to have a concentrated solution wherein the ratios by weight A/B/C are 1/1/1.

Under stirring, the concentrated solution is added to a preformed gel based on xanthan rubber so as to obtain the following final composition (% by weight):

| | |
|---|---|
| Perfluoropolyether phosphate (Fomblin ® HC/P2-1000) | 5.0 |
| Ethanol | 5.0 |
| Xanthan rubber (Rodicare ® T by Rhodia) | 1.5 |
| Water as suff. to | 100 |

A stable, transparent gel with pH=2.48 is obtained.

EXAMPLE F2

4 aliquots of the formulation of Example 2 are weighed and with a sterilized spatula are transferred into 4 test-tubes. Each test-tube is inoculated with one of the four microorganisms listed in Example 1, following the procedure as described in said Example.

The results are reported in Table 1 and show that the perfluoropolyether phosphate is active in reducing all the microorganisms which have been inoculated.

EXAMPLE 3

Formulation Gel

A gel for the hand protection based on xanthan rubber has been prepared starting from the same concentrated solution of Example 2, adding said solution to a preformed gel in the weight ratios for obtaining the following final composition (% by weight):

| | |
|---|---|
| Perfluoropolyether phosphate (Fomblin ® HC/P2-1000) | 1.0 |
| Ethanol | 1.0 |
| Xanthan rubber (Rodicare ® T by Rhodia) | 1.5 |
| Water as suff. to | 100 |

A stable, transparent gel with pH 3.44 is obtained.

EXAMPLE F3

The gel of Example 3 is inoculated as described in Example F2 for the gel of Example 2.

The results are reported in the following Table 2. The same comments made for Table 1 are valid.

ESEMPIO 4 (comparative)
Formulation Gel

A gel for the hand protection based on xanthan rubber as in Example 3 has been prepared, starting from the same concentrated solution of Example 2, but adding a perfluoropolyether phosphate with a fluorinated chain having a number average molecular weight 2,000 (Fomblin® HC/P2–2000) obtaining the following final composition (W by weight):

| | |
|---|---|
| Perfluoropolyether phosphate (Fomblin ® HC/P2-2000) | 1 |
| Ethanol | 1 |
| Xanthan rubber (Rodicare ® T by Rhodia) | 1.5 |
| Water as suff. to | 100 |

A stable, transparent gel with pH 3.79 is obtained.

EXAMPLE F4 (COMPARATIVE)

The gel of Example 4 (comparative) is inoculated as described in Example F2 for the gel of Example 2.

The results are reported in the following Table 3. In the Table the abbreviation n.d. means that at the indicated time the counting has not been made since no longer important for the experiment purposes. The Table shows that the perfluoropolyether phosphate of formula (I) having a number average molecular weight of the fluorinated chain of 2,000 has no preserving activity.

EXAMPLE 5 (COMPARATIVE)

Lactic acid dissolved in not much water is added to a preformed gel based on xanthan rubber, adding ethanol so as to have a gel having a pH very close to that of the previous Example 3, having the following composition (W by weight):

| | |
|---|---|
| Lactic acid sufficient amount to have pH = | 3.95 |
| Xanthan rubber | 1.5 |
| Ethanol | 0.5 |
| Water as suff. to | 100 |

A stable, transparent gel having pH=3.95 is obtained.

EXAMPLE F5 (COMPARATIVE)

On the preparation of Example 5 the inoculum is repeated as described in Example F2.

The obtained data are reported in Table 4 and show that under these conditions the preparation remains contaminated from gram positive bacteria, from *P. aerugininosa* and from *C. albicans*.

EXAMPLE 6

Gel formulation

A Carbomer gel (Carbopol® Ultrez 10) is prepared from a solution at 50% of perfluoropolyether phosphate of formula (I) having a molecular weight of the perfluorinated chain of about 1,200 (Fomblin® HC/P2–1000) component A) in pentan-1,2-diol (INCI naming: pentylene glycol) component B), to which an amount of water is added so as to have a concentrated solution wherein the ratios by weight A/B/C are 1/1/1.

Under stirring, the concentrated solution is gradually added to a preformed gel based on Carbomer (INCI name). When the addition is over, the stirring is continued for further 10 minutes. Sodium hydroxide is added so as to restore the pH of the preformed gel, obtaining the following final composition (% by weight):

| | |
|---|---|
| Perfluoropolyether phosphate (Fomblin ® HC/P2-2000) | 1 |
| Carbomer | 0.3 |
| Pentylene glycol | 1 |
| Sodium hydroxide as suff. to pH 5.57 | |
| Water as suff. to | 100 |

A stable gel with pH 5.57 is obtained.

EXAMPLE F6

The gel of Example 6 is inoculated as described in Example F2 for the gel of Example 2.

The results are reported in the following Table 5. The same comments made for Table 1 are valid.

EXAMPLE 7

Formulation Emulsion/Gel

The formulation is prepared by starting from an aqueous phase formed by Carbomer (INCI naming) (Carbopol® Ultrez 10) dispersed in water. To this aqueous dispersion an oily phase formed by octyl palmitate and mineral oil wherein acrylate C/10–30 alkylacrylate crosslinked polymer (INCI Acrylates C/10–30 Alkyl Acrylate Cross Polymer naming) Pemulen® TR-1 (BF Goodrich) is added under strong stirring. It is neutralized by sodium hydroxide so as to have a pH 5.5, obtaining a white stable emulsion.

A concentrated solution of perfluoropolyether phosphate is separately prepared as in the previous Example 6.

The concentrated solution is added under slow stirring to the previous emulsion and it is neutralized again with sodium hydroxide (few drops) obtaining a pH of 5.3.

A white stable emulsion, having the following composition as percentage by weight, is obtained:

| | |
|---|---|
| Perfluoropolyether phosphate (Fomblin ® HC/P2-2000) | 1 |
| Carbomer | 0.15 |
| Pemulen ® TR-1 | 0.20 |
| Octyl palmitate | 10 |

-continued

| Mineral oil | 10 |
|---|---|
| Pentylenic glycol | 1 |
| Sodium hydroxide as suff. to pH 5.30 | |
| Water as suff. to | 100 |

EXAMPLE F7

The formulation of Example 7 is inoculated as described in Example F2 for the gel of Example 2.

The results are reported in the following Table 6. The same comments made for Table 1 are valid.

EXAMPLE 8 (COMPARATIVE)

A formulation emulsion/gel of the same composition as that of Example 7 is prepared but without perfluoropolyether phosphate. Said formulation has pH of 6.24.

EXAMPLE F8 (COMPARATIVE)

The formulation of Example 8 is inoculated as described in Example F2 for the gel of Example 2.

The results are reported in Table 7 and they show that in absence of perfluoropolyether phosphate the composition remains contaminated.

TABLE 1

Decrease in the time of the colonies of *E. coli, S. aureus, P. aeruginosa* and *C. albicans*, inoculated in the preparation of the gel of Example 2. The data reported in the Table are expressed in units forming colonies/ml (UFC/ml)

| | 20 min. UFC/ml × $10^5$ | 1 UFC/ml × $10^3$ | days 7 UFC/ml | 14 UFC/ml | 28 UFC/ml |
|---|---|---|---|---|---|
| *Escherichia coli* | 6.4 | 10 | <10 | <10 | <10 |
| *Staphylococcus aureus* | 7.9 | 3 | <10 | <10 | <10 |
| *Pseudomonas aeruginosa* | 4.0 | 4 | <10 | <10 | <10 |
| *Candida albicans* | 8.6 | 0.6 | $9 \times 10^2$ | 10 | <10 |

TABLE 2

Decrease in the time of the colonies of *E. coli, S. aureus, P. aeruginosa* and *C. albicans*, inoculated in the preparation of the gel of Example 3. The data reported in the Table are expressed in units forming colonies/ml (UFC/ml)

| | 20 min. UFC/ml × $10^7$ | 1 UFC/ml × $10^3$ | days 7 UFC/ml | 14 UFC/ml | 28 UFC/ml |
|---|---|---|---|---|---|
| *Escherichia coli* | 40 | 3 | $1.6 \times 10^3$ | <10 | <10 |
| *Staphylococcus aureus* | 3 | 4 | <10 | <10 | <10 |
| *Pseudomonas aeruginosa* | 7 | 20 | <10 | <10 | <10 |
| *Candida albicans* | 0.05 | 6 | $2 \times 10^2$ | 10 | <10 |

TABLE 3

Decrease in the time of the colonies of *E. coli, S. aureus, P. aeruginosa* and *C. albicans*, inoculated in the preparation of the gel of the Example 4 (comparative) wherein Foblin P2-2000 has been used. The data reported in the Table are expressed in units forming colonies/ml (UFC/ml)

| | 20 min. UFC/ml × $10^6$ | 1 UFC/ml × $10^5$ | giorni 7 UFC/ml × $10^3$ | 14 UFC/ml × $10^3$ | 28 UFC/ml |
|---|---|---|---|---|---|
| *Escherichia coli* | 1 | 2.8 | 5.3 | <0.01 | n.d |
| *Staphylococcus aureus* | 40 | 8.4 | 3 | 1.1 | n.d |
| *Pseudomonas Aeruginosa* | 2 | <0.01 | 0.01 | 4 | n.d. |
| *Candida albicans* | 0.3 | 0.1 | 80 | 320 | n.d. |

TABLE 4

Decrease in the time of the colonies of *E. coli, S. aureus, P. aeruginosa* and *C. albicans*, inoculated in the preparation of the gel of the Example 5 (comparative) which contains lactic acid instead of perfluoropolyether phosphate. The data reported in the Table are expressed in units forming colonies/ml (UFC/ml)

| | 20 min. UFC/ml × $10^7$ | 1 UFC/ml × $10^7$ | days 7 UFC/ml | 14 UFC/ml | 28 UFC/ml |
|---|---|---|---|---|---|
| *Escherichia coli* | 6.8 | 4.6 | <10 | <10 | n.d. |
| *Staphylococcus aureus* | 3.6 | 2.1 | $3 \times 10^5$ | $5.9 \times 10^5$ | n.d. |
| *Pseudomonas Aeruginosa* | 6 | 1.1 | $6.8 \times 10^2$ | $4.1 \times 10^5$ | n.d. |
| *Candida albicans* | 0.02 | 0.008 | $8 \times 10^4$ | $2.2 \times 10^5$ | n.d. |

TABLE 5

Decrease in the time of the colonies of *E. coli, S. aureus, P. aeruginosa* and *C. albicans*, inoculated in the preparation of the gel of Example 6. The data reported in the Table are expressed in units forming colonies/ml (UFC/ml)

| | 20 min. UFC/ml × $10^7$ | 1 UFC/ml × $10^3$ | days 7 UFC/ml | 14 UFC/ml | 28 UFC/ml |
|---|---|---|---|---|---|
| *Escherichia coli* | 40 | 3 | $1.6 \times 10^3$ | <10 | <10 |
| *Staphylococcus aureus* | 3 | 4 | <10 | <10 | <10 |
| *Pseudomonas aeruginosa* | 7 | 20 | <10 | <10 | <10 |
| *Candida albicans* | 0.05 | 6 | $2 \times 10^2$ | 10 | <10 |

TABLE 6

Decrease in the time of the colonies of *E. coli, S. aureus, P. aeruginosa* and *C. albicans*, inoculated in the preparation emulsion/gel of Example 7. The data reported in the Table are expressed in units forming colonies/ml (UFC/ml)

| | 20 | days | | | |
|---|---|---|---|---|---|
| | min. UFC/ml × 10$^7$ | 1 UFC/ml × 10$^5$ | 7 UFC/ml | 14 UFC/ml | 28 UFC/ml |
| *Escherichia coli* | 2.3 | 7.2 | <100 | <10 | <10 |
| *Staphylococcus aureus* | 3.1 | 7.6 | <100 | <10 | <10 |
| *Pseudomonas aeruginosa* | 1.8 | 0.47 | <100 | <10 | <10 |
| *Candida albicans* | 1.7 | 3.2 | <10 | <10 | <10 |

TABLE 7

Decrease in the time of the colonies of *E. coli, S. aureus, P. aeruginosa* and *C. albicans* inoculated in the preparation emulsion/gel of the Example 8 (comparative) which does not contain perfluoropolyether phosphate. The data reported in the Table are expressed in units forming colonies/ml (UFC/ml)

| | 20 | days | | | |
|---|---|---|---|---|---|
| | min. UFC/ml × 10$^7$ | 1 UFC/ml × 10$^6$ | 7 UFC/ml × 10$^2$ | 14 UFC/ml | 28 UFC/ml |
| *Escherichia coli* | 3.4 | 1.9 | 31 | n.d. | n.d. |
| *Staphylococcus aureus* | 4.4 | 1.7 | 8.9 | n.d. | n.d. |
| *Pseudomonas Aeruginosa* | 6.1 | 3.2 | 160 | n.d. | n.d. |
| *Candida albicans* | 0.91 | 0.16 | 2.1 | n.d. | n.d. |

What is claimed is:

1. A method for protecting liquid formulations from bacterial contamination, wherein said method comprises adding to said formulations component A):

a (per)fluoropolyether phosphate of general formula:

$$R_f\text{—}[CF_2CH_2\text{—}O\text{—}L\text{—}P(O)(OZ_1)(OZ_2)]_I \quad (I)$$

wherein I=1 or 2;

L is a bivalent linking group $(CHR_1CHR_2O)$, wherein $R_1$, $R_2$ equal to or different from each other are selected from H, $CH_3$; n is an integer in the range 1–50;

$Z_1$ equal to or different from $Z_2$ is selected from the group consisting of H, alkaline or ammonium cation, di- or tri-alkanolammonium cation wherein alkanol comprises from 1 to 20 C atoms, di- or tri- or tetra-alkylammonium cation wherein alkyl comprises from 1 to 20 C atoms, or $R_f$—$CF_2CH_2$—O—L—;

Rf represents a (per)fluoropolyether chain having number average molecular weight in the range from about 400 to about 1,800, said (per)fluoropolyether chain comprising repeating units selected from one or more of the following:

a) —$(C_3F_6O)$—;
b) —$(CF_2CF_2O)$—;
c) —$(CFL_0O)$—, wherein $L_0$=—F, —$CF_3$;
d) —$CF_2(CF_2)_{z'}CF_2O$—, wherein z' is an integer 1 or 2;
e) —$CH_2CF_2CF_2O$—.

2. The method according to claim 1, wherein when in the (per)fluoropolyether phosphate of general formula (I) $R_f$ is monofunctional (I=1), an end group is perfluoroalkyl selected from the group consisting of $CF_3O$, $C_2F_5O$, $C_3F_7O$; optionally one fluorine atom of said end groups can be replaced by one chlorine or hydrogen atom, said end groups are selected from the group consisting of $Cl(C_3F_6O)$ and $H(C_3F_6O)$.

3. The method according to claim 1, wherein the (per)fluoropolyether chain $R_f$ is selected from the following structures:

1) —$(CF_2O)_a$—$(CF_2CF_2O)_b$— with b/a comprised between 0.3 and 10, extremes included, a being an integer different from 0;

2) —$(CF_2$—$(CF_2)_{z'}$—$CF_2O)_{b'}$— wherein z' is an integer equal to 1 or 2;

3) —$(C_3F_6O)_r$—$(C_2F_4O)_b$—$(CFL_0O)_t$—, with r/b =0.5–2.0 (r+b)/t=10–30, b and t being integers different from 0;

4) —$(OC_3F_6)_r$—$(CFL_0O)_t$—$OCF_2$—$R'_f$—$CF_2O$—$(C_3F_6O)_r$—$(CFL_0O)_t$—

5) —$(CF_2CF_2CH_2O)_{q'}$—$R'_f$—O—$(CH_2CF_2CF_2O)_{q'}$— wherein:

$R'_f$ is a fluoroalkylene group from 1 to 4 carbon atoms;
$L_0$ is selected between F, $CF_3$;

6) —$(C_3F_6O)_r$—$OCF_2$ $R'_fCF_2O$—$(C_3F_6O)_r$— wherein in said formulas:

—$(C_3F_6O)$— can represent units of formula:

—$CF(CF_3)$ $CF_2O$— and/or —$(CF_2$—$CF(CF_3)O)$— a, b, b',q', r, t, are integers, the sum of which is such that $R_f$ shows values of number average molecular weight $M_n$ in the range from about 400 to about 1,800.

4. Use according to claim 3, wherein the (per)fluoropolyether chain $R_f$ is selected from the following structures:

—$(CF_2O)_a$—$(CF_2CF_2O)_b$—;
—$(C_3F_6O)_r$—$(C_2F_4O)_b$—$(CFL_0O)_t$—;
—$(C_3F_6O)_r$—$(CFL_0O)_t$—;

wherein $L_0$ and the a,b,r,t indexes have the above indicated value.

5. Use according to claims 3 and 4, wherein $R_f$ is —$(CF_2O)_a$—$(CF_2CF_2O)_b$— and the a and b indexes have the above indicated values.

6. The method according to claim 1, wherein in the (per)fluoropolyether of formula (I) L=$(CH_2$—$CH_2O)_n$ with n=1–3; $z_1$ equal to or different from $z_2$ is H, $NH_4$, or an alkaline metal cation; 1=2.

7. Use according to claims 3-6, wherein the (per)fluoropolyether of general formula (I) has the following formulas:

$$\text{—}CF_3\text{—}O(CF_2CF(CF_3)O)_r(CF_2O)_a\text{—}CF_2\ CH_2\ (OCH_2CH_2)_nO\text{—}PO(OH)_2 \quad (II)$$

wherein r/a=0.5–2.0 and n=1–2;

$$\text{—}CF_2\text{—}O(CF_2CF_2O)_b(CF_2O)_a\text{—}CF_2\text{—}[CH_2\text{—}(OCH_2CH_2)_nO\text{—}PO(OH)_2]_2 \quad (III)$$

wherein b/a=0.5–3.0 and n=1–2;
wherein a, b and r have the above mentioned meaning.

8. The method according to claim 1, wherein the formulations contain a solvent component B) selected from the group consisting of linear or branched when possible alcohols, from 2 to 3 carbon atoms and methyl ethers thereof; linear or branched glycols from 2 to 6 carbon atoms or linear or branched mono alkyletherified wherein the alkyl group ranges from 1 to 4 carbon atoms; dimethoxymethane and acetone.

9. The method according to claim 8, wherein the solvent is ethanol, ethylene glycol, isopropanol, propanol, acetone, methoxyethanol, propylene glycol, propan-1, 2-diol, dimethoxy methane, methoxy-isopropanol, diethylene glycol, butan-1, 4-diol, diethylenglycolmonoethylenether, pentan-1, 2-diol, diethylenglycol monoethylether, dipropylenglycol, dipropylenglycol monomethylether or dipropylenglycol monoethylether.

10. The method according to claim 1, wherein the percentage by weight of the (per)fluoropolyether phosphate of formula (I) component A) in the compositions for topical use is in the range 0.01–10%.

11. The method according to claim 8, wherein the percentage by weight of the solvent component B) is in the range 0.01–10%.

12. The method according to claim 8, wherein in the formulations for topical use a 1:1 ratio by weight between the solvent component B) and the (per)fluoropolyether phosphate of formula (I) component A) is used.

* * * * *